United States Patent
Chaney et al.

[11] Patent Number: 5,818,047
[45] Date of Patent: Oct. 6, 1998

[54] DETECTOR FOR EXPLOSIVE SUBSTANCES

[75] Inventors: Raymond J Chaney, Berkeley; David N Batchelder, Leeds; Richard J Lacey, St Albans, all of United Kingdom

[73] Assignee: Renishaw PLC, Gloucestershire, United Kingdom

[21] Appl. No.: 793,196
[22] PCT Filed: Aug. 21, 1995
[86] PCT No.: PCT/GB95/01979
  § 371 Date: Feb. 20, 1997
  § 102(e) Date: Feb. 20, 1997
[87] PCT Pub. No.: WO96/06346
  PCT Pub. Date: Feb. 29, 1996

[30] Foreign Application Priority Data

Aug. 20, 1994 [GB] United Kingdom .................. 9416889
Dec. 24, 1994 [GB] United Kingdom .................. 9426241
May 5, 1995 [GB] United Kingdom .................. 9509264

[51] Int. Cl.⁶ .......................... G01N 21/65; G01N 33/22
[52] U.S. Cl. .................. 250/341.8; 250/339.11; 356/301
[58] Field of Search ............. 250/341.1, 341.8, 250/339.11, 339.12; 356/301

[56] References Cited

U.S. PATENT DOCUMENTS 5,112,127 5/1992 Carrabba et al. .
5,377,044 12/1994 Tomono et al. .

FOREIGN PATENT DOCUMENTS

A 455-516 11/1991 European Pat. Off. .
A 0-543-578 5/1993 European Pat. Off. .
5-256782 10/1993 Japan ..................................... 356/301
WO 90-07108 6/1990 WIPO .

OTHER PUBLICATIONS

Hodges, Colin M. and Jacqueline Akhavan. "The use of Fourier Transform Raman spectroscopy in the forensic identification of illicit drugs and explosives." *Spectrochimica Acta*, vol. 46A, pp. 303–307, 1990.

Cheng, C. et al., "In Situ Detection and Identification of Trace Explosives by Raman Microscopy," *Journal of Forensic Sciences*, Jun. 1994, pp. 31–37.

Akhavan, J., "Analysis of high–explosive samples by Fourier transform Raman spectroscopy," *Spectrochimica Acta*, vol. 47A, No. 9/10, 1991, pp. 1246–1250.

Carver, F.W.S. et al., "Detection of Nitro Compounds on Silica Gel and Carbon by Non–Resonant Raman Spectroscopy," *Journal of Raman Spectroscopy*, vol. 14, No. 6, 1983, pp. 410–414.

Vo–Dunh et al., "Surface. Enhanced Raman Spectrometry For Trace Organic Analysis", Anal. Chem., vol. 56, No. 9, Aug. 1984, pp. 1667–1670.

*Primary Examiner*—Edward J. Glick
*Attorney, Agent, or Firm*—Oliff & Berridge, PLC

[57] ABSTRACT

The presence of Semtex plastic explosive in a sample such as a fingerprint is detected by Raman spectroscopy. RDX and PETN, the active chemical ingredients of Semtex, have strong Raman peaks at 885 cm$^{-1}$ and 874 cm$^{-1}$ respectively. Consequently, both these peaks can be detected in a Raman spectroscopic system by employing a filter having a narrow passband centered on 880 cm$^{-1}$ and with a bandwidth of 20 cm$^{-1}$. Such a filter is used in a Raman system used to scan airport boarding cards, or in a Raman microscope which produces images of fingerprints.

13 Claims, 5 Drawing Sheets

DETECTOR FOR EXPLOSIVE SUBSTANCES

FIELD OF THE INVENTION

This invention relates to apparatus for detecting explosive substances. In some embodiments, at least, the invention relates to the detection of the explosive components of the plastic explosive Semtex.

DESCRIPTION OF PRIOR ART

European Patent Application No. EP 455516 (British Aerospace) describes a security procedure for use in airports and the like. Each passenger boarding an aircraft is given a boarding card in the normal way, which he or she subsequently hands in at a checkpoint, prior to boarding the aircraft. If that person has been handling explosives or other contraband material, traces of that material will be present on the boarding card after he or she has handled it. At the checkpoint, the boarding card is analysed in order to detect these traces. EP 455516 discloses several possible methods for chemical analysis in order to detect the traces of material. These include mass spectrometry, gas chromatography, and ion mobility spectrometry. None of these techniques has proved practicable, however, for various reasons. For example, the explosive components of the plastic explosive Semtex have an extremely low vapour pressure which makes them extremely difficult to detect by "sniffer" technology. Furthermore, the techniques suggested tend to destroy the sample, so that the boarding card is no longer available as evidence against the passenger concerned.

Raman spectroscopy is a known technique for analysing and identifying materials. See for example International Patent Application WO90/07108 (Renishaw) and European Patent Application No. EP 543578 (Renishaw).

The plastic explosive Semtex has two active chemical ingredients: cyclotrimethylene-trinitramine or RDX, and pentaerythritol-tetranitrate or PETN. RDX and PETN are present in the explosive as transparent micrometer sized crystals bound together by an amorphous waxy material. Several workers have previously reported the Raman spectra of RDX and PETN, for example obtained by Fourier Transform Raman spectroscopy. See for example J. Akhavan, "Analysis of High-Explosive Samples by Fourier Transform Raman Spectroscopy", Spectrochimica Acta, Vol 47A, No.9/10 1991, pages 1247–1250. However, such studies have been conducted under laboratory conditions, and do not address the practicalities of attempting to produce apparatus which can detect the presence of a plastic explosive such as Semtex in a relatively short space of time, and possibly contaminated by other substances, such as required in the field.

SUMMARY OF THE INVENTION

The invention follows from the results of further work which we have performed, analysing Semtex samples using the Raman analysis apparatus described in EP 543578. It should be noted that the RDX and PETN components of Semtex occur in varying proportions in commercial samples of Semtex. Moreover, many of the peaks in the Raman spectra of RDX and PETN are polarisation dependent. Since most of the microscopic particles of Semtex which might be found in a field sample such as a fingerprint consist of individual single crystals, we find that the intensities of the polarised Raman bands depend upon the angle differences between the polarisation plane of the laser illumination and the crystalline orientation. Our studies show that the frequencies remain the same, however.

In particular, from our studies we have found that RDX has a strong peak at 885 $cm^{-1}$ and PETN has a strong peak at 874 $cm^{-1}$, irrespective of polarisation.

According to the present invention, a method for detecting an explosive substance in a field sample comprises illuminating the sample, thereby producing a spectrum of Raman scattered light, and filtering the Raman spectrum thus produced using a narrow bandpass filter covering both 885 $cm^{-1}$ and 874 $cm^{-1}$, and detecting the light thus filtered. From the above discussion, it will be appreciated that if a sample containing Semtex is analysed, then the method may detect either or both of the RDX band at 885 $cm^{-1}$ and/or the PETN band at 874 $cm^{-1}$, irrespective of the proportion of these materials present in the Semtex.

The invention also provides several different, configurations of apparatus for performing this method.

BRIEF DESCRIPTION OF THE DRAWINGS

Preferred embodiments of the invention will now be described with reference to the accompanying drawings, wherein.

DESCRIPTION OF PREFERRED EMBODIMENTS

Figure 1A:
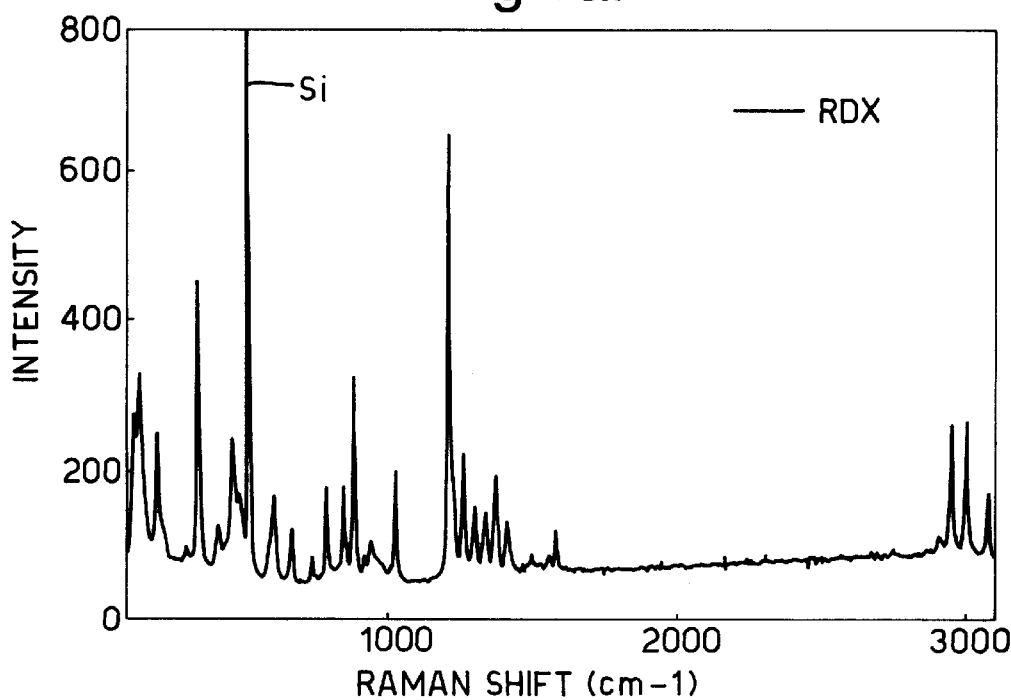
FIGS. 1a) and b) show Raman spectra of RDX and PETN respectively, on a silicon wafer.
Figure 1B:
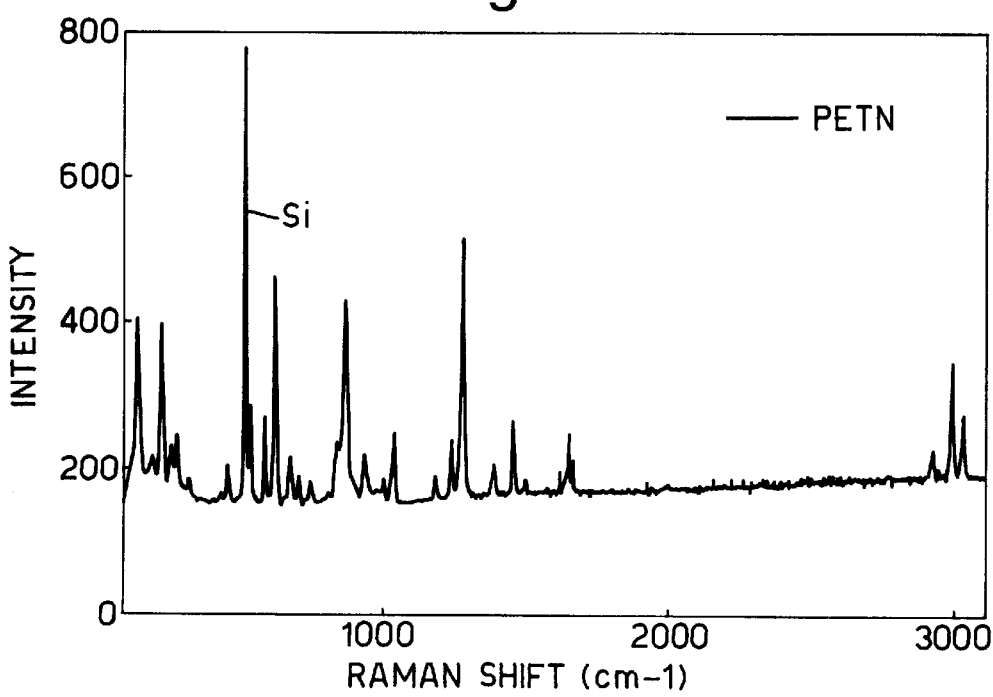
Figure 2A:
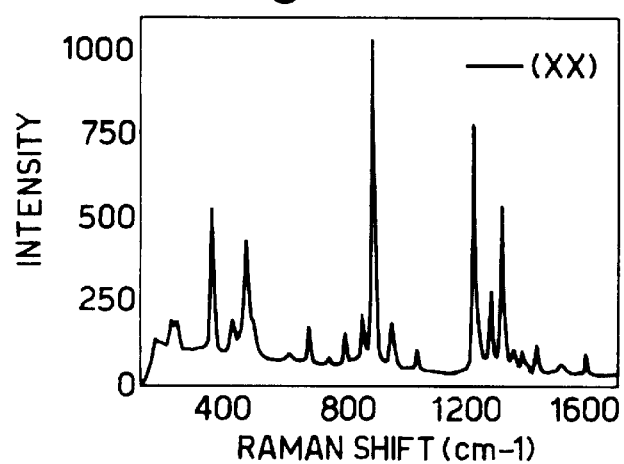
FIGS. 2a)–2f) show polarised Raman spectra of an RDX crystal at different orientations.
Figure 2B:
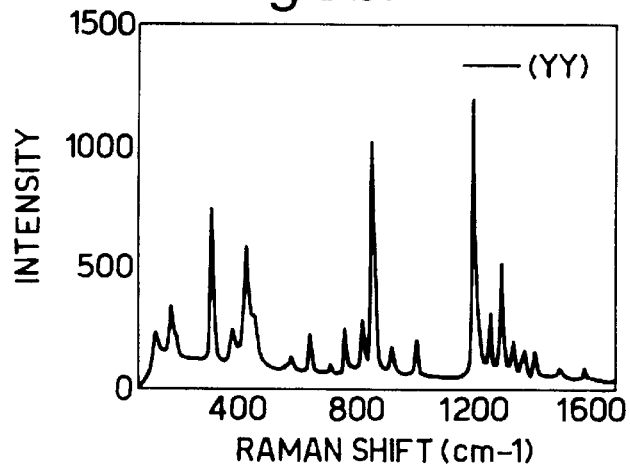
Figure 2C:
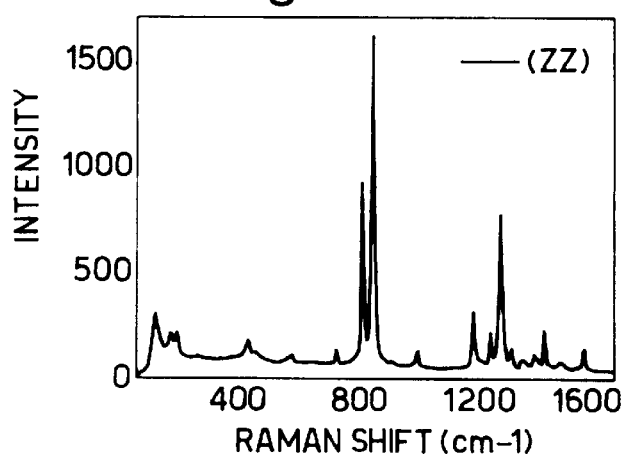
Figure 2D:
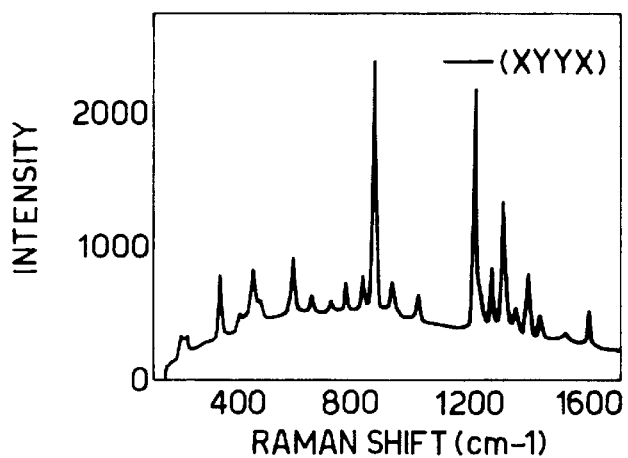
Figure 2E:
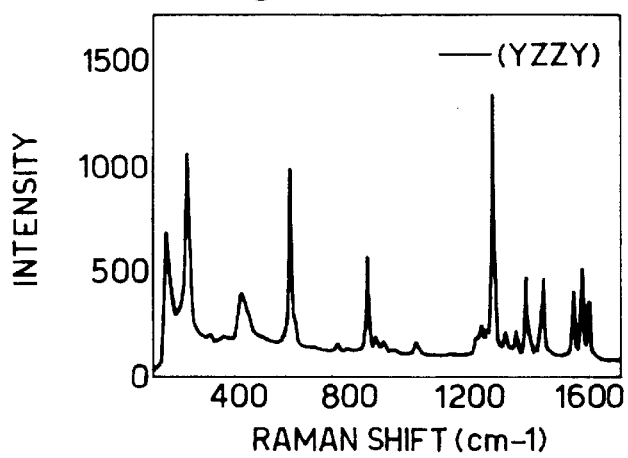
Figure 2F:
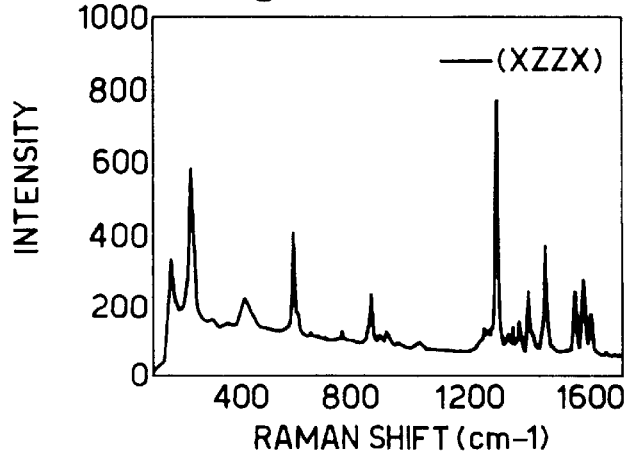

Typical Raman spectra from RDX and PETN crystals, several microns on a side, deposited on a silicon wafer are shown in FIGS. 1A and 1B, where a) is for RDX and b) for PETN. The measurements were made using the apparatus of EP 543578, with a 25 mW HeNe laser emitting at 632.8 nm. A X20, NA=0.45, microscope objective was used. The amount of power reaching the sample was about 5 mW, which corresponds to an energy density of $2\times10^9$ $W/m^2$.

Acquisition time for the above two spectra was 5 s. Both RDX and PETN appear to have large Raman scattering cross sections, making the Raman spectra easy to acquire. We have also tested a 514.5 nm line Ar+ laser with the same samples and obtained essentially identical results. The spectra are similar in appearance to those acquired at lower spectral resolution using the FT Raman technique with much greater laser powers and long recording times.

We have demonstrated that a plastic explosive like Semtex can be identified by simply taking a Raman spectrum or a Raman band image. Table 1 is a list of all the Raman bands appearing in the spectra shown by FIG. 1A and 1B. The relative peak intensities are shown by letter indexes: S means strong, M moderate and W weak; the V prefix means very. P indicates the peak is polarised. On first inspection the Raman spectra from different RDX particles often look somewhat different because most of the particles are individual single crystals. For a single crystal sample, the intensities of the polarised Raman bands depend upon the angle differences between the polarisation plane of the laser and the crystalline orientation. The frequencies remain the same, however.

TABLE 1

| RDX (cm$^{-1}$) | | PETN (cm$^{-1}$) | |
|---|---|---|---|
| 129 | S | | |
| 152 | S | 147 | S |
| | | 194 | W |
| 207 | S | | |
| 226 | W | 229 | S |
| | | 260 | M |
| | | 280 | M |
| 304 | VW | | |
| | | 321 | W |
| 345 | VS, P | | |
| 413 | M | | |
| 463 | S | 458 | M |
| 487 | M | | |
| | | 539 | MS |
| 589 | W | 589 | MS |
| 606 | M | | |
| | | 625 | VS |
| 668 | M | 677 | M |
| | | 705 | M |
| 737 | W | | |
| | | 751 | W |
| 787 | M | | |
| 849 | M | 840 | M |
| | | 874 | VS |
| 885 | S | | |
| 922 | W | | |
| 944 | W | 941 | M |
| | | 1005 | VW |
| 1031 | S, P | 1033 | VW |
| | | 1045 | M |
| | | 1195 | W |
| 1217 | VS, P | | |
| 1235 | M, P | | |
| | | 1253 | M |
| 1272 | S, P | 1279 | M |
| | | 1294 | VS |
| 1312 | S, P | | |
| 1350 | M, P | | |
| 1390 | M, P | | |
| | | 1405 | W |
| 1426 | M, P | | |
| | | 1471 | M |
| 1509 | VW | 1512 | VW |
| 1573 | VW | | |
| 1595 | W, P | | |
| | | 1631 | VW |
| | | 1662 | M |
| | | 1675 | M |
| 2909 | W | 2917 | W |
| 2953 | M | | |
| | | 2990 | M |
| 3006 | M | | |
| | | 3024 | M |
| 3079 | M | | |

Polarised Raman spectra taken from a RDX single crystal are shown in FIGS. 2A to 2F. The crystal was grown in a laboratory and came out rectangular in shape, approximately 1×2×5 mm$^3$ in size. We defined the X,Y and Z axes accordingly; therefore the longest dimension of the crystal was along Z and the two flat surfaces in the YZ planes. Theoretical analysis shows that the intensity of Raman scattered light is proportional to the square of the dipole moment induced in the sample by the incident radiation. This dipole moment u is written as:

$$u = a\, E \quad (1)$$

or $$u_x = a_{xx}E_x + a_{xy}E_y + a_{xz}E_z$$
$$u_y = a_{yx}E_x + a_{yy}E_y + a_{yz}E_z \quad (2)$$
$$u_z = a_{zx}E_x + a_{zy}E_y + a_{zz}E_z$$

where E is the electric field of the incident laser beam and a the polarisability tensor. By orienting the RDX crystal sample with the microscope sample stage and arranging a polarisation analyser in front of the spectrometer, nine Raman spectra were obtained. Each of these spectra reflects the contribution from one of the nine elements of the polarisability tensor, i.e. XX,YY,ZZ,XY,YX,XZ,ZX,YZ or ZY etc. Only the six independent spectra are shown here because of the fact that $a_{xy}=a_{yx}$, $a_{xz}=a_{zx}$ and $a_{yz}=a_{zy}$. In addition to proving that the RDX particles are single crystals, this type of study provides detailed information about the symmetries of the vibrational modes.

As can be seen from FIGS. 1A to 1B and FIGS. 2A to 2F and Table 1, RDX has a strong band at 885 cm$^{-1}$ and PETN a strong band at 874 cm$^{-1}$. These bands remain strong, independent of polarisation and crystalline orientation. As a result of these studies, we have realised that the components of the Semtex material such as Semtex-H can be detected by using a narrow passband filter, the passband being centred at 880 cm$^{-1}$ and the bandwidth being (say) 20 cm$^{-1}$ in order to cover both of these bands at 885 cm$^{-1}$ and 874 cm$^{-1}$.

Figure 3:
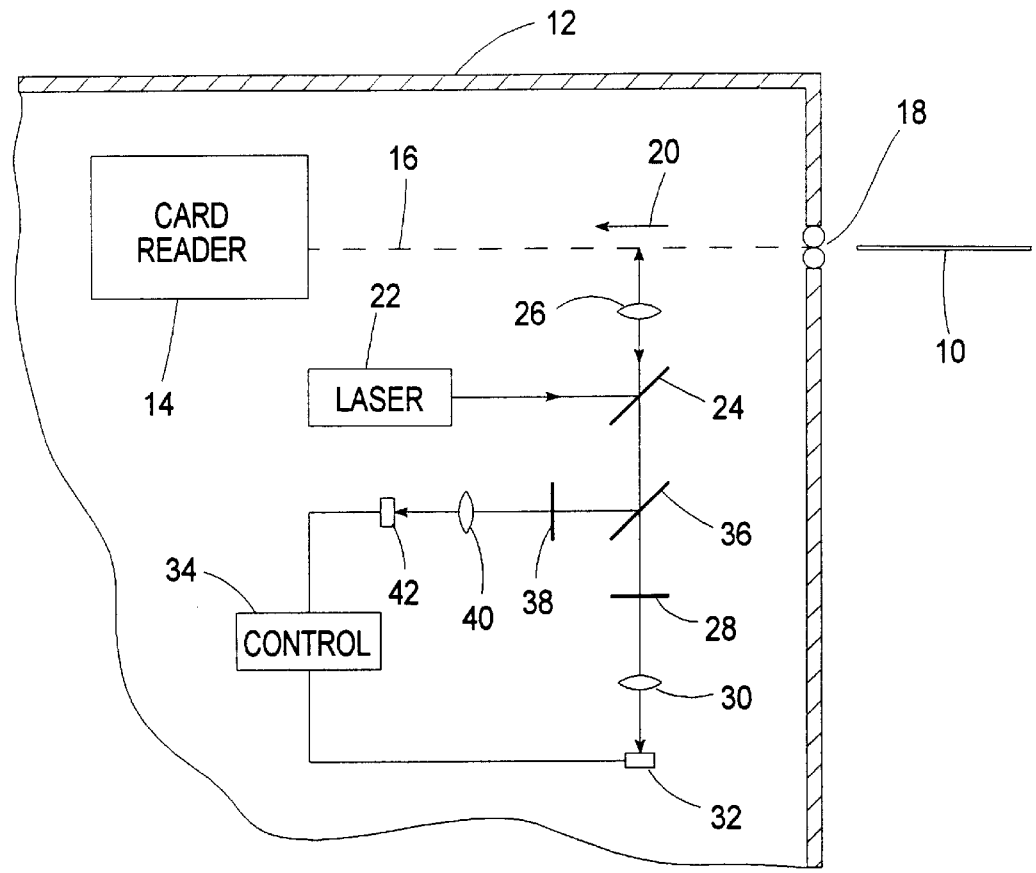
FIG. 3 is a schematic diagram of a boarding card reader, for example for use in airports.

FIG. 3 shows how a conventional airport boarding card reader may be modified to incorporate such a detector. When a passenger checks in at the airport, he or she is given a boarding card 10 in the conventional way. If he or she has previously handled Semtex explosive, then trace particles will remain on his or her hands and will be transferred to the boarding card 10 during normal handling. Subsequently, at a suitable checkpoint such as the airport gate prior to boarding the aircraft, the passenger is required to feed the boarding card 10 into the card reader shown in FIG. 3.

As shown schematically in FIG. 3, the boarding card reader comprises a housing 12, within which is provided a conventional card reading device 14. The card reader has a conventional transport mechanism for transporting the card in the direction of arrow 20 along a transport path 16 to the card reading device 14 from an entrance slot 18 of the housing. The card reading device 14 performs functions such as identifying each passenger in order to determine whether any passenger has not shown up. It may return to the passenger a small portion of the card, containing details such as seat number etc., but preferably retains the majority of the card. This means that, in the event that Semtex is detected, the card is retained for further analysis which can provide confirmation, and for use as evidence if required.

As the boarding card 10 is transported along the transport path 16 it is scanned by light from a laser 22. Many types of laser are suitable, including gas lasers such as Helium-Neon, or a suitably stabilised and filtered semi-conductor laser diode. A dichroic filter 24 reflects light of the laser wavelength through 90°, and it is focused by a lens or lens system 26 onto the card 10 as it passes along the path 16. Since it is preferable to scan the whole area of the card 10, or a large proportion of it, the lens system 26 may include a cylindrical lens giving a line focus transversely across the width of the card as it moves in the direction of the arrow 20. The same lens system 26 collects scattered light from the illuminated line. This passes back to the dichroic filter 24, which rejects reflected and Rayleigh scattered light having the same wavelength as the exciting laser 22, but transmits any Raman scattered light. The Raman scattered light passes via a narrow bandpass filter 28 and is focused by a lens 30 onto a detector 32, which may be an avalanche photodiode.

The filter 28 has a narrow passband of about 20 cm$^{-1}$ and is centred at about 880 cm$^{-1}$. As discussed above, therefore, the detector 32 will react if any particles of RDX or PETN are present on the boarding card 10, because the filter will pass the strong Raman bands at 874 cm$^{-1}$ and 885 cm$^{-1}$.

However, the detector 32 will not react to scattered light at any other wavenumber. In FIG. 3, the filter 28 is shown normal to the optical path, but it may be at an angle to the normal if required to tune it to 880 cm$^{-1}$.

The output from the detector 32 is taken to a control 34, which may include a computer for controlling various parts of the apparatus, and which gives an appropriate indication if a signal above a given threshold is received from the detector 32. Preferably, the control 34 should be able to perform background subtraction, i.e. determining the height of any peak detected by the 880 cm$^{-1}$ filter 28 above any background. This can be important if the boarding card is likely to carry materials which give broadband luminescence or fluorescence, either from the material of the boarding card itself or from dirt or grease which it has acquired during handling. To achieve background subtraction, part of the scattered light may be reflected by a beam splitter 36 placed before the filter 28, to a further narrowband filter 38, lens 40 and detector 42. These are similar to the components 28,30, 32, except that the filter 38 is tuned to a narrow band to one side of the 880 cm$^{-1}$ band, e.g. 810 cm$^{-1}$, at which Semtex has little or no Raman scattering. The output of the detector 42 is taken to the control 34, where it is subtracted from the signal from the detector 32 either by appropriate software in the computer, or by a dedicated electronic circuit such as a comparator. The control 34 then gives the appropriate indication if the background-subtracted signal rises above a predetermined threshold.

In FIG. 3, the beam splitter 36 may be a simple 50:50 beam splitter. However, to prevent the loss of scattered light available for detection, preferably it is an edge filter, having a sharp cut-off between the respective bands of the filters 28,38. This ensures that all the light in the 880 cm$^{-1}$ band passes through to the filter 28, while all the light in the adjacent band is reflected to the filter 38. Indeed, instead of an edge filter, the filter 36 may itself be designed to pass only the 20 cm$^{-1}$ wide band centred on 880 cm$^{-1}$ directly to the detector 32 (without the need for a separate filter 28), reflecting all other light to the background filter 38. Alternatively, the filter 36 may be a notch filter which transmits all the scattered light through to the filter 28, except for the narrow band required for background subtraction which is reflected directly to the detector 32 (without the need for the filter 38).

Our tests have shown that Raman apparatus such as that described can be successful in detecting extremely small particles of Semtex, e.g. about 1 μm$^3$, weighing about 1 picogram, in a few seconds. Our tests simulated real life conditions in which we made "impure" samples with fingertips which were cross contaminated by both Semtex and other greasy substances. Depending upon the sensitivity required, and the false alarm rate which is deemed acceptable, however, it may be desirable to reduce the speed at which the boarding card 10 passes along the transport path 16, compared with the speed used in conventional boarding card readers. A further possibility is to coat the card material with a thin layer of a substance such as silver, gold or copper, having a suitably roughened surface. With such an appropriate surface, molecules of the RDX or PETN material adsorbed onto the roughened surface may exhibit surface-enhanced Raman scattering (SERS) which increases the Raman scattering by a very large factor.

It may also be desirable to ensure that the boarding cards are made of a non-fluorescent card material. An alternative to using non-fluorescent card is to use a laser 22 which produces light in the far red or in the infra-red region of the spectrum. Excitation with such wavelengths reduces considerably or eliminates the fluorescence problem.

Of course, other optical arrangements than that shown in FIG. 3 can be used. For example, a suitable optical arrangement may illuminate and collect Raman scattered light from both sides of the card simultaneously.

Figure 4:
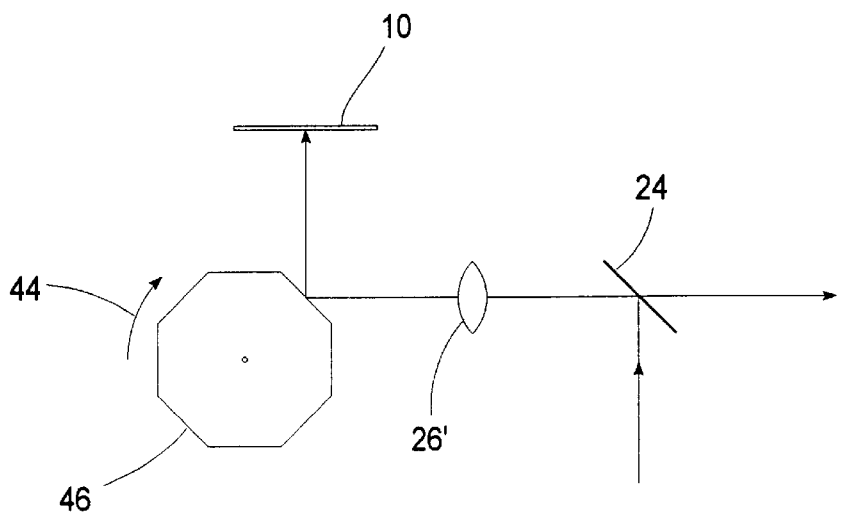
FIG. 4 is a schematic diagram of a modified scanning device for use in the card reader of FIG. 3.

FIG. 4 shows a modification of the scanning arrangement for the boarding card reader of FIG. 3. Here, the boarding card 10 is seen in transverse cross-section, looking in the direction of the arrow 20 in FIG. 3. The cylindrical lenses necessary in the lens system 26 to produce a line focus across the card may not be the most efficient way to collect the maximum amount of Raman scattered light. Consequently, FIG. 4 shows a modified lens system 26' which produces a point focus on the card 10, and which has a greater collection efficiency for the Raman scattered light. The light is focused onto the card 10 after reflection by a polygonal block 46, each face of which has a mirror surface. The block 46 is continuously rotated as indicated by the arrow 44, by a motor (not shown). This causes the laser spot to scan transversely across the card 10, at a faster rate than the lengthwise scan provided by the movement of the card along the transport path 16. Scattered light from the card passes back via the mirror face of the block 46 and the lens system 26', into a similar optical detection system as shown in FIG. 3.

The systems described in FIGS. 3 and 4 merely detect the presence of Semtex at some point on the card 10. One particular advantage of the Raman analysis technique is that it is non-destructive. Hence, if Semtex is detected, the card can be retained for further analysis and for use as evidence. Obviously, such systems can be modified for detecting Semtex on other surfaces such as tickets, identity cards, passports, etc., and may be used in situations other than an airport boarding card reader, e.g. at the entrances to public buildings, government offices and the like. The non-destructive nature of the Raman analysis lends itself to such situations, since the ticket, card etc can be handed back to the holder after analysis.

Furthermore, the detector and associated components 32–42 of FIG. 3 may be used in conjunction with a hand-held fibre optic probe head such as described in U.S. Pat. Nos. 5,377,004 (Owen) and 5,112,127 (Carrabba). Light from the laser 22 is fed down on optical fibre to the probe head, and Raman scattered light is fed back via another optical fibre to the components 32—42. Such a hand-held fibre optic probe head may then be used to sense the presence of Semtex on a wide variety of articles, including direct sensing of a suspect's hands, or of luggage which is about to be loaded onto an aircraft. Indeed, with appropriate miniaturisation, the detector components 32–42 and the various filters and lenses may be built into a hand-held probe unit, along with an appropriate objective lens and a semiconductor laser diode. To assist with positioning of the probe head relative to the article to be sensed, the probe may be provided with appropriate stand-off or other positioning accessories.

Figure 5:
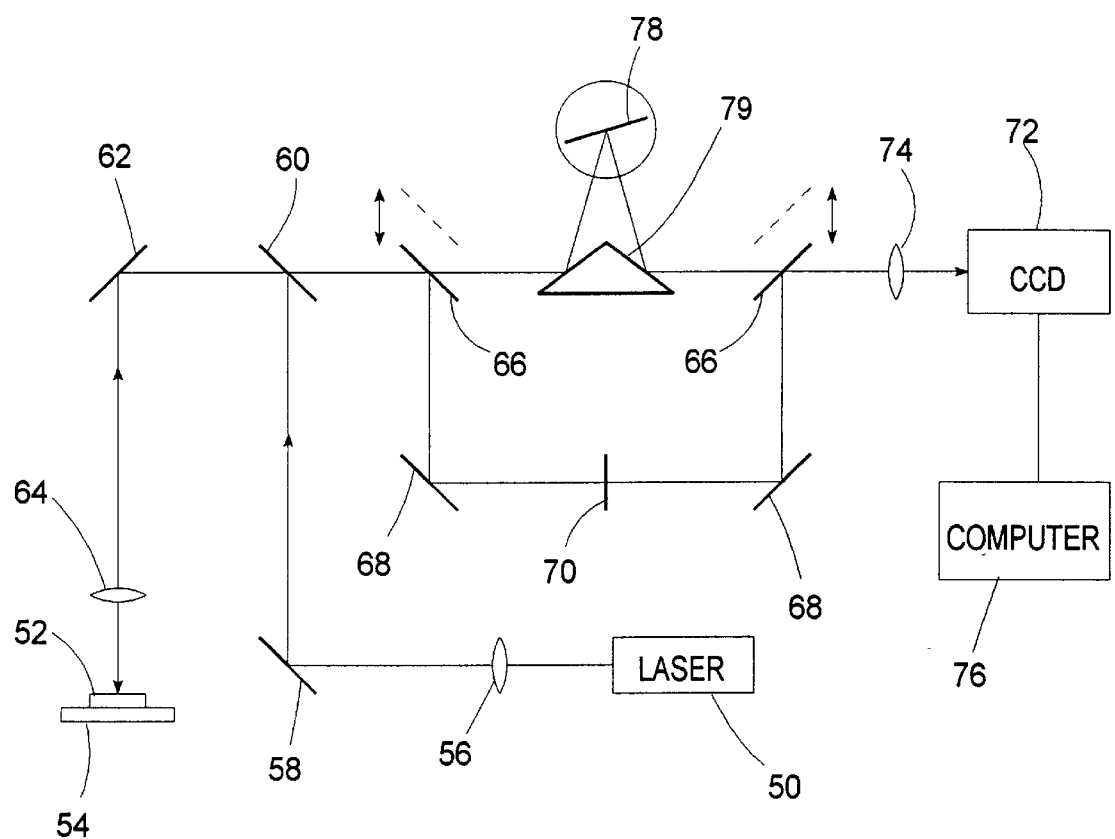
FIG. 5 is a schematic diagram of further apparatus for analysing field samples such as fingerprints.

In some situations it may be desirable to analyse a sample in more detail than is permitted by the equipment shown in FIGS. 3 and 4. This may be done with apparatus such as shown in FIG. 5, which is similar to that shown in EP 543578, to which reference should be made for more detail. A sample 52 placed on a microscope stage 54 is illuminated by light from a laser 50, via a lens system 56, mirror 58, dichroic filter 60, mirror 62 and microscope objective lens 64. If it is desired to form an image of an area of the sample, then the lens 56 is adjusted so as to defocus the laser beam on the sample 52 illuminating the required area. Raman scattered light is collected by the microscope objective 64, and passes back through the dichroic filter 60 (which rejects reflected and Rayleigh scattered light having the same wavelength as the laser, as previously). The Raman scattered light then passes through a filter 70, via mirrors 66,68. The filter 70 is a narrow passband filter centred on 880 cm$^{-1}$ and with a bandwidth of 20 cm$^{-1}$ as previously, in order to detect the RDX and PETN components of Semtex. A two-dimensional image of the illuminated area of the sample, in light of the band centred on 880 cm$^{-1}$, is then focused by a lens 74 onto a suitable two-dimensional detector such as a charge-coupled device (CCD) 72. This image is acquired and displayed by a computer 76, which also controls other parts of the apparatus as required. For example, the computer 76 can perform background subtraction for the same reason as described above, by tilting the filter 70 slightly to retune it to an adjacent passband. The computer 76 then acquires another, background image, and subtracts the data for each pixel of the background image from the corresponding data for the image in the 880 cm$^{-1}$ band.

FIG. 5 also shows that the apparatus may have a separate mode of operation explained in more detail in EP 543578, which is useful for confirming the presence of RDX or PETN if detected in any particular part of the image. The lens 56 may be refocused to produce illumination at the single point of interest in the image, moving the microscope stage 54 as necessary. The mirrors 66 are removed from the optical path, so that the Raman scattered light is now reflected via a prism 79 to a diffraction grating 78. This disperses a spectrum of the Raman scattered light at the point of interest across the surface of the CCD 72, enabling positive confirmation that it is RDX and/or PETN by comparison with the spectra shown in FIGS. 1 and 2.

Of course, the apparatus shown in FIG. 5 may be modified for various different applications. The full system as shown in FIG. 5 would be more appropriate for use in a forensic laboratory, where skilled personnel are present who can identify the spectra produced by the diffraction grating 78. Alternatively, to produce a system which might be of use in a police station, the diffraction grating 78, the prism 79 and the mirrors 66,68 may be omitted, the filter 70 being placed in the straight through position between the dichroic filter 60 and the lens 74. An unskilled operator can then easily produce images of fingerprints in the 20 cm$^{-1}$ band around 880 cm$^{-1}$, which will show the presence of particles of Semtex in the fingerprint.

Rather than providing background subtraction by adjustment of the tuning of the filter 70, the same effect may be achieved by exchanging the filter 70 for another filter with the appropriate passband for background detection. Furthermore, a useful facility is to be able to remove the filter 70, so that an image of the fingerprint or other sample may be formed on the CCD taken in white light introduced into the microscope. The ability to compare a white light image of a fingerprint with one taken in the 880 cm$^{-1}$ band is particularly advantageous, because it enables one to see that any traces of explosive which are found are indeed associated with the fingerprint. This eliminates the possibility that the fingerprint might be on a substrate which had previously been contaminated with the explosive, and improves the value of the forensic evidence produced by the technique.

As can be seen from FIG. 2, although the 885 cm$^{-1}$ band of RDX is always present, it is to some extent polarisation dependent. The peak at 874 cm$^{-1}$ for PETN is not polarisation dependent. These facts can be used to distinguish between RDX and PETN if desired. A polarisation filter is placed in the optical path of the Raman scattered radiation after the dichroic filter 24,60, and is adjusted to see whether or not the detected intensity in the 880 cm$^{-1}$ band alters.

A further modification of the apparatus of FIG. 5 (with or without the diffraction grating 78) is to provide a filter 70 which is exchangeable for another filter, tuned to one of the other peaks shown in FIGS. 1 and 2, e.g. a 533 cm$^{-1}$ peak of RDX. Alternatively, one filter 70 may be tunable to both peaks. An image is taken in the Raman scattered light of each of the peaks 533 cm$^{-1}$ and 885 cm$^{-1}$ of RDX, and a background is subtracted from each (using images taken at, say, 500 cm$^{-1}$ and 810 cm$^{-1}$ respectively). The resulting two images are combined by the computer 76 using AND logic to produce a final image which only shows those regions that are producing both the 533 and 885 cm$^{-1}$ peaks. This leads to a more positive identification of RDX in the fingerprint. The same technique may be used in a non-imaging system, e.g. by providing further filters and beam splitters in the system of FIG. 3. In a similar fashion, other substances than Semtex can be positively identified from two or more characteristic Raman peaks.

The dichroic filters 24,60 in FIGS. 3,4 and 5 may be multi-layer dielectric filters. Alternatively, holographic notch or edge filters may be used, as described in EP 543578, and may be used at a low angle of incidence such as 10° or 11° to improve their polarisation independence. Rugate filters may be substituted for holographic filters. The filters 28,38,70 may also be of any of these types.

The paper by C. Cheng et al, "In-Situ Detection and Identification of Trace Explosives by Raman Microscopy", Journal of Forensic Sciences, JFSCA, Vol 40, No. 1, January 1995, pages 31–37 is incorporated herein by reference. This paper was published after the priority date of the present patent application.

We claim:

1. Apparatus for detecting an explosive material in a sample, comprising:

a light source for illuminating the sample to cause the production of Raman scattered light;

a detector for detecting Raman scattered light received from the sample; and a filter between the sample and the detector, the filter passing to the detector only light in a band which includes 874 cm$^{-1}$ and 885 cm$^{-1}$, said band being sufficiently narrow that light substantially greater than 885 cm$^{-1}$ or substantially less than 874 cm$^{-1}$ is not passed to the detector.

2. Apparatus according to claim 1, wherein the sample is in the form of a document, an area of which is scanned by the light source, detector and filter.

3. Apparatus according to claim 2, in which the document is transported past the light source, detector and filter.

4. Apparatus according to claim 2, including a lens arranged to produce a line focus of light from the light source across the document.

5. Apparatus according to claim 2, including a device which scans a spot of light from the light source across the document.

6. Apparatus according to claim 2, wherein said document is a card.

7. Apparatus according to claim 1, wherein the detector detects a two-dimensional image of an area of the sample.

8. Apparatus according to claim 1, including means for detecting a spectrum of Raman scattered light, in addition to said filter.

9. Apparatus according to claim 1, wherein the filter has a bandwidth of about 20 cm$^{-1}$, centred on about 880 cm$^{-1}$.

10. A method for detecting an explosive material in a sample, comprising:

illuminating the sample with a light source to cause the production of Raman scattered light;

detecting the Raman scattered light received from the sample with a detector, wherein a filter is placed between the sample and the detector to pass to the detector only light in a band which includes 874 $cm^{-1}$ and 885 $cm^{-1}$, the band being sufficiently narrow that light substantially greater than 885 $cm^{-1}$ or substantially less than 874 $cm^{-1}$ is not passed to the detector.

11. A method according to claim 10, wherein the sample is in the form of a document, an area of which is scanned by the light source, detector and filter.

12. A method according to claim 11, in which the document is transported past the light source, detector and filter.

13. A method according to claim 10, wherein the filter has a bandwidth of about 20 $cm^{-1}$, centered on about 880 $cm^{-1}$.

* * * * *